US011833165B2

(12) United States Patent
Hennet et al.

(10) Patent No.: US 11,833,165 B2
(45) Date of Patent: *Dec. 5, 2023

(54) SYNTHETIC COMPOSITION AND METHOD FOR TREATING IRRITABLE BOWEL SYNDROME

(71) Applicant: Glycom A/S, Hørsholm (DK)

(72) Inventors: Thierry Hennet, Otelfingen (CH); Bruce McConnell, La Tour de Peilz (CH); Emma Elison, Hjärup (SE); Louise Kristine Vigsnæs, København NV (DK)

(73) Assignee: GLYCOM A/S, Hørsholm (DK)

( * ) Notice: Subject to any disclaimer, the term of this patent is extended or adjusted under 35 U.S.C. 154(b) by 142 days.

This patent is subject to a terminal disclaimer.

(21) Appl. No.: 17/341,039

(22) Filed: Jun. 7, 2021

(65) Prior Publication Data
US 2021/0308158 A1  Oct. 7, 2021

Related U.S. Application Data

(63) Continuation of application No. 15/897,099, filed on Feb. 14, 2018, now Pat. No. 11,026,959, which is a continuation of application No. 15/034,593, filed as application No. PCT/DK2015/050332 on Oct. 29, 2015, now abandoned.

(30) Foreign Application Priority Data

Oct. 29, 2014 (DK) .......................... PA 2014 70663

(51) Int. Cl.
A61K 31/702 (2006.01)
A61K 31/7004 (2006.01)
A61K 31/7012 (2006.01)
A61P 1/04 (2006.01)
A23L 33/21 (2016.01)
A23C 9/20 (2006.01)

(52) U.S. Cl.
CPC ............ A61K 31/702 (2013.01); A23C 9/206 (2013.01); A23L 33/21 (2016.08); A61K 31/7004 (2013.01); A61K 31/7012 (2013.01); A61P 1/04 (2018.01); A23V 2002/00 (2013.01)

(58) Field of Classification Search
CPC ............ A61K 31/702; A61K 31/7004; A61K 31/7012; A61K 2300/00
USPC ..................................................... 514/23, 61
See application file for complete search history.

(56) References Cited

U.S. PATENT DOCUMENTS

| 4,663,321 | A | 5/1987 | Bock et al. | |
| 10,751,354 | B2 | 8/2020 | Vigsnæs et al. | |
| 11,026,959 | B2* | 6/2021 | Hennet ................ | A61K 31/702 |
| 11,040,049 | B2* | 6/2021 | McConnell ........ | A61K 31/7016 |
| 11,040,050 | B2 | 6/2021 | Vigsnæs et al. | |
| 11,050,050 | B1* | 6/2021 | Lai ........................ | H01M 4/661 |
| 2007/0185094 | A1 | 8/2007 | Lattmann et al. | |
| 2012/0028911 | A1 | 2/2012 | Shebuski et al. | |
| 2012/0171165 | A1* | 7/2012 | Buck ........................ | A61P 1/00 |
| | | | | 514/23 |
| 2012/0171166 | A1 | 7/2012 | Chow et al. | |
| 2012/0172319 | A1 | 7/2012 | Chow et al. | |
| 2013/0195803 | A1 | 8/2013 | German et al. | |
| 2013/0251844 | A1 | 9/2013 | Sprenger | |
| 2013/0315990 | A1 | 11/2013 | Bode | |
| 2014/0249103 | A1 | 9/2014 | Buck et al. | |
| 2016/0346303 | A1 | 12/2016 | Thierry et al. | |
| 2018/0169122 | A1 | 6/2018 | Hennet et al. | |
| 2018/0177809 | A1 | 6/2018 | McConnell et al. | |
| 2018/0185398 | A1 | 7/2018 | Vigsnaes et al. | |
| 2021/0308159 | A1 | 10/2021 | McConnell et al. | |
| 2021/0386766 | A1 | 12/2021 | Vigsnaes et al. | |

FOREIGN PATENT DOCUMENTS

| JP | 2007512220 A | 5/2007 |
| JP | 2012532195 A | 12/2012 |
| WO | 0104341 A1 | 1/2001 |
| WO | 2004026257 A2 | 4/2004 |
| WO | 2007101862 A1 | 9/2007 |
| WO | 2009131537 A1 | 10/2009 |
| WO | 2010115934 A1 | 10/2010 |
| WO | 2010115935 A1 | 10/2010 |
| WO | 2011005681 A8 | 1/2011 |
| WO | 2011100979 A1 | 8/2011 |
| WO | 2011100980 A1 | 8/2011 |
| WO | 2012007588 A9 | 1/2012 |
| WO | 2012009315 A2 | 1/2012 |
| WO | 2012092155 A1 | 7/2012 |
| WO | 2012092160 A2 | 7/2012 |

(Continued)

OTHER PUBLICATIONS

Gavini et al., Microbial Ecology in Health and Disease, 2001, 13, 40-45.*
Rockova, S. "Inter-species differences in the growth of bifidobacteria cultured on human milk oligosaccharides", Folia Microbiologica, 2012, vol. 57, No. 4, Apr. 11, 2021, pp. 321-324.
Heitkemper, M. "Update on Irritable Bowel Syndrome Program of Research", J Korean Academy of Nursing vol. 43 No. 5, 579-586, http://dx.doi.org/10.4040/jkan.2013.43.5.579, Sep. 23, 2013, pp. 579-586.
Sela et al,. "Nursing our microbiota: molecular linkages between bifidobacteria and milk oligosaccharides", Trends in Microbiology, 2010, pp. 298-307.

(Continued)

Primary Examiner — Ganapathy Krishnan
(74) Attorney, Agent, or Firm — Kunzler Bean & Adamson; Thomas Briscoe

(57) ABSTRACT

The application relates to a method for treating a patient with irritable bowel syndrome (IBS), the method comprising administering to the patient one or more neutral human milk oligosaccharides (HMOs) selected from 2'-fucosyllactose (2'-FL), 3-fucosyllactose (3-FL), difucosyllactose (DFL), lacto-N-fucopentaose I, lacto-N-tetraose (LNT), lacto-N-neotetraose (LNnT), and combinations thereof.

19 Claims, No Drawings

(56) References Cited

FOREIGN PATENT DOCUMENTS

| WO | 2012/106665 A2 | 8/2012 |
|---|---|---|
| WO | 2012113404 A1 | 8/2012 |
| WO | 2012113405 A1 | 8/2012 |
| WO | 2012127410 A1 | 9/2012 |
| WO | 2012155916 A1 | 11/2012 |
| WO | 2012156897 A1 | 11/2012 |
| WO | 2012156898 A1 | 11/2012 |
| WO | 2013044928 A1 | 4/2013 |
| WO | 2013091660 A1 | 6/2013 |
| WO | 2013139344 A1 | 9/2013 |
| WO | 2013148134 A1 | 10/2013 |
| WO | 2013154725 A1 | 10/2013 |
| WO | 2015077233 A1 | 5/2015 |
| WO | 2015157098 A1 | 10/2015 |
| WO | 2013161693 A1 | 12/2015 |

OTHER PUBLICATIONS

Gavini et al., "Differences in the Distribution of Bifidobacterial and Enterobacterial Species in Human Faecal Microflora of Three Different (Children, Adults, Elderly) Age Groups", Microbial Ecology in Health and Disease 2001; 13, 40-45.

Michael Camilleri, "Peripheral Mechanisms in Irritable Bowel Syndrome", N Engl J. Med. 367; 17, Oct. 25, 2012, NEJM.org, pp. 1626-1635.

Thapar et al., "Diarrhoea in children: an interface between developing and developed countries", The Lancet, vol. 363, Feb. 21, 2004, www.lancet.com, pp. 641-653.

Jeffery, I. et al., An irritable bowel syndrome subtype defined by species-specific alterations in faecal microbiota, GUT 2012, 61:997-1006, published on Dec. 16, 2011, doi: 10.1136/gutjnl-2011-301501, pp. 997-1006.

L. O'Mahony et al., "Lactobacillus and Bifidobacterium in Irritable Bowel Syndrome: Symptom Responses and Relationship to Cytokine Profiles", Gatroenterology 2005;128:pp. 541-551.

E. Elison et al., "Oral supplementation of healthy adults with 2 !-O-fucosyllactose and lacto-N-neotetraose is well tolerated and shifts the intestinal microbiota", British Journal of Nutrition, Aug. 22, 2016, pp. 1-13.

G. Gibson et al., "The International Scientific Association for Probiotics and Prebiotics (ISAPP) consensus statement on the definition and scope of prebiotics", Nature Reviews | Gatroenterology & Hepatology, vol. 14, Aug. 2017, pp. 491-502.

Urashima, T. et al., "Mild Oligosaccharides", Nutrition and Diet Resarch Progress, Nova Biomedical Books, New York, (2011).

Kerckhoffs, A. et al., "Lower bifidobacteria counts in both duodenal mucosa-associated and fecal microbiota in irritable bowel syndrome patients", World J. Gastroenterol, 15(23):2887-2892, doi:10.3748/wjg.15.2887, (Jun. 21, 2009).

Schoepfer, A. et al., "Antibodies to flagellin indicate reactivity to bacterial antigens in IBS patients", Neurogastroenterol Motil, vol. 20, pp. 1110-1118, doi:10.1111/j.1365-2982.2008.01166.x, (2008).

J. Yang, "Lactose intolerance in irritable bowel syndrome patients with diarrhoea: the roles of anxiety, activation of the innate mucosal immune system and visceral sensitivity", Alimentary Pharmacology and Therapeutics, 2014, 39, pp. 302-311.

D. Barile et al., "Human milk and related oligosaccarides as prebiotics", Biotechnology, Feb. 19, 2013, pp. 214-219.

M. Haarman et al., Quantitative Real-Time PCR Assays to Identify and Quantify Fecal Bifidobacterium Species in Infants Receiving a Prebiotic Infant Formula, Applied and Environmental Microbiology, vol. 71, No. 5, May 2005, pp. 2318-2324.

N. Sprenger et al., "Longitudinal change of selected human milk oligosaccharides and association to infants' growth, an observatory, single center, longitudinal cohort study", PLOS ONE, Feb. 9, 2017, pp. 1-15.

Chaturvedi, P., "Milk Oligosaccharide profiles by reversed-phase HPLC of their perbenzoylated derivatives", Analytical Biochemistry, vol. 251, pp. 89-97; whole document doi:10.1006/abio.1997.2250, (Sep. 1997).

Qin, J. et al., "A human gut microbial gene catalogue established by metagenomic sequencing", Nature, vol. 464, pp. 69-67, doi:10.1038/nature08821, (Mar. 4, 2010).

Silk, D. et al., "Clinical trial: the effects of a trans-galactooligosaccharide prebiotic on faecal microbiota and symptoms in irritable bowel syndrome", Alimentary Pharmacology & Therapeutics, doi:10.1111/j.1365-2036.2008.03911.x, (Nov. 28, 2008).

Walker M. et al., "Duodenal mastoctosis, eosinophilia and intaepithelial lymphocytosis ans possible disease markers in the irritable lowel syndrome and functional dyspepsia", Alimentary Pharmacology & Therapeutics, 29(7_765-773, doi:10.111/j.1365-2036.2009.03937.x, (Apr. 2009).

Buhner, S. et al., "Mast cell-nerve axis with a focus on the human gut", Biochimica et Biophysica Acta, 1822, pp. 35-92, doi:10.1016/j.bbadis.2001.06.004, (2012).

Sikandar, S. et al., "Visceral pain-the ins and Outs, the Ups and Downs", Curr Opin Support Palliat Care, 6(1):17-26, doi:10.1097/SPC.0b013e32834f6ec9, (Mar. 2012).

Kim, G. et al., "Methanobrevibacter smithii is the predominant methanogen in patients with constipation-predominant BM and methane on breath", Dig Dis Sci, vol. 57, pp. 3213-3218, doi: 10.1007/s10620-012-2197-1, (2012).

Bassett, J. et al., "A review of irritable bowel syndrome and an update on therapeutic approaches", Informa Healthcare, Expert Opin. Pharmacother, 9(7):1129-1143, doi:10.1517/14656560802048902, (2008).

Longstreth, G. et al., "Functional bowel disorders", Gastrenterologia vol. 130, pp. 1480-1491, doi:10.1053/j.gastro.2005.11.061, (2006).

Spiller R. et al., "Postinfectious irritable bowel syndrome", Gastroenterology, vol. 136, pp. 1979-1988, doi:10.1053/j.gastro.2009.02.074, (2009).

Guilatre M., et al., "Diarrheoa-predominant IBS patients show mast cell activation and hyperplasia in the jejunum", Gut, vol. 56, pp. 203-209, doi:10.1136/gut.2006.100594, (2007).

Spiller, R. et al., "Guidelines on the irritable bowel syndrome: mechanisms and practical management", Gut, vol. 56, pp. 1770-1798, doi:10.1136/gut.2007.119446, (2007).

Staudacher, H. et al., "Comparision of symptom response following advice for a diet low in fermentable carbohydrates (FODMAPs) verus standard dietary advice in patients with irritable bowel syndrome", Journal of Human Nutrition and Dietetics, vol. 24, pp. 487-495 (2011).

Zhang, L. et al., "Mast cells and irritable bowl syndrome: from the bench to the bedside", Journal of Neurogastroenterology and Motility, 22:2:181-192, (Apr. 2016).

Shulman R. et al., "Increased gastrointestinal permeability and gut inflammation in children with functional abdominal bain and irritable bowel syndrome", J. Pediatr., 153(5):646-650, doi: 10.1016/j.jpeds.2008.04.062, (Nov. 2008).

Ohman, L. et al., "Crosstalk at the mucosal border: importance of the gut microenvironment in IBS", Nat, Rev. Gastroenterol., vol. 12, pp. 36-49, doi:10. 1038/nrgastro.2014.200, (Jan. 2015).

Haarman et al., "Quantitative Real-Time PCR Assays to Identify and Quantify Fecal Bifidobacterium Species in Infants Receiving a Prebiotic Infant Formula", Applied and Environmental Microbiology, May 2005, p. 2318-2324.

Elison et al., "Oral Supplementation of healthy adults with 2'-O-fucosyllactose and lacto-N-neotetraose is well tolerated and shifts the intestinal microbiota", British Journal of Nutrition, Aug. 22, 2016, pp. 1-13.

Gibson et al., "The International Scientific Association for Probiotics and Prebiotics (ISAPP) consensus statement on the definition and scope of prebiotics", Nature Reviews, Gastroenterology & Hepatology, Jun. 14, 2017, pp. 1-12.

\* cited by examiner

SYNTHETIC COMPOSITION AND METHOD FOR TREATING IRRITABLE BOWEL SYNDROME

CROSS-REFERENCES TO RELATED APPLICATIONS

This application is continuation of U.S. patent application Ser. No. 15/897,099 titled Synthetic Composition And Method For Treating Irritable Bowel Syndrome and filed on Feb. 14, 2018, which is a continuation application of and claims priority to U.S. patent application Ser. No. 15/034,593 titled Synthetic Composition And Method For Treating Irritable Bowel Syndrome and filed on May 5, 2016 for Thierry Hennet et al., and claims the priority to PCT/DK2015/050332 titled Synthetic Composition And Method For Treating Irritable Bowel Syndrome and filed on Oct. 29, 2015 for Thierry Hennet and claims priority to Denmark Application No. PA 2014 70663, each of which is incorporated herein by reference to the extent permitted by applicable patent law and rules.

FIELD

This disclosure relates generally to compositions and methods for the treatment of irritable bowel syndrome (IBS).

BACKGROUND

Irritable bowel syndrome is a clinically heterogeneous disorder of human, particularly adult, patients with chronic symptoms such as abdominal pain, abdominal discomfort, abdominal bloating, fatigue, and changes in bowel movement patterns, such as patterns of loose or more frequent bowel movements, diarrhoea, and constipation. Routine clinical tests on patients typically show no abnormalities, although their bowels may be more sensitive to certain stimuli, such as balloon insufflation testing. The worldwide prevalence of IBS is about 10-20% (Longstreth et al. Gastroenterology 130, 1480 (2006)) but may be higher in certain countries. The causes of IBS are unknown but disruptions of the brain-gut axis, acute gastrointestinal infections, small intestinal bacterial overgrowths, antibiotic usages and dysbiosis are thought to be important risk factors (Kim et al. Digest. Dis. Sci. 57, 3213 (2012)). Other risk factors are young age, prolonged fever, anxiety, and depression. Chronic low-grade inflammation commonly occurs in IBS patients, but there are otherwise little or no observable clinical manifestations.

Diagnosis of IBS is difficult. No biomarker-based tests can be performed to diagnose LBS. Diagnosis generally involves excluding conditions that produce IBS-like symptoms and then following a procedure to categorize a patient's symptoms. Ruling out parasitic infections, lactose intolerance, and celiac disease is recommended for all patients before a diagnosis of IBS is made. Once diagnosed, patients are usually classified in accordance with the Rome III criteria into four symptom subtypes based on stool consistency: diarrhoea predominant (IBS-D), constipation predominant (IBS-C), mixed subtype (IBS-M) with alternating episodes of both diarrhoea and constipation, and unsubtyped IBS (IBS-U).

There is no cure for IBS and current treatments focus on attempting to relieve symptoms. Treatments take various forms such as dietary adjustments, medication, and psychological interventions. Patient education and good doctor-patient relationships are also important. However, most treatment is unsatisfactory and most patients continue to experience chronic pain, fatigue, and other symptoms. While IBS has no direct effect on life expectancy, its high prevalence and significant effects on quality of life make it a condition with a high social cost. The general hopelessness associated with IBS is a source of frustration for both patients and health care practitioners treating them.

A recent development in IBS treatment has been the FODMAP diet. This diet requires patients to restrict the intake of FODMAP carbohydrates. These are Fermentable Oligo-, Di-, Monosaccharides And Polyols which are poorly absorbed in the proximal small intestine, osmotically active, and fermented by intestinal bacteria with hydrogen production. Adherence to this diet has resulted in symptom improvements for some patients (Staudacher et al. J. Hum. Nutr. Diet. 24, 487 (2011)). However, some of the FODMAP carbohydrates are beneficial fibres, and foods that contain them are common, highly nutritious fruits, vegetables, and legumes. There has remained, however, a need for a generally safe and effective way for further improving the symptoms of IBS patients generally.

SUMMARY

A method is disclosed that includes selecting a non-infant human patient with irritable bowel syndrome (IBS) experiencing one or more IBS symptoms. In various examples, the method further includes selecting an amount of one or more neutral human milk oligosaccharides (HMOs) chosen from the group consisting of 2'-fucosyllactose (2'-FL), 3-fucosyllactose (3-FL), difucosyllactose (DFL), lacto-N-fucopentaose I, lacto-N-tetraose (LNT), lacto-N-neotetraose (LNnT), and combinations thereof, the amount effective for increasing a relative abundance of *Bifidobacterium adolescentis* in the gastrointestinal microbiota of the non-infant human patient.

In certain examples, the method further includes increasing the relative abundance of *Bifidobacterium adolescentis* in the gastrointestinal microbiota of the non-infant human patient and reducing the likelihood of the non-infant human patient experiencing the one or more IBS symptoms by administering a daily dose of the selected amount of the one or more neutral HMOs to the non-infant human patient.

In various examples, the non-infant human patient has undergone treatment with an antibiotic to reduce bacteria that negatively affect the IBS, and wherein the non-infant human patient has not consumed the antibiotic in a three-month period prior to the administering of the chosen one or more HMOs. In certain examples, the one or more IBS symptoms are chronic symptoms selected from abdominal pain, abdominal discomfort, abdominal bloating, change in bowel movement patterns, diarrhea, and constipation. In some examples, the daily dose of the chosen one or more neutral HMOs administered to the non-infant human patient is from about 2.5 g to about 10 g.

In certain examples, the method further includes administering with the selected amount of the chosen one or more neutral HMOs, one or more sialylated HMOs selected from 6'-sialyllactose (6'-SL) and 3'-sialyllactose (3'-SL). In some examples, administering chosen one or more neutral HMOs includes administering a mixture of: one or more fucosylated neutral HMOs selected from 2'-FL, 3-FL, DFL, and LNFP-I; and one or more non-fucosylated neutral HMOs selected from LNT and LNnT. In various examples, mass ratio of the fucosylated neutral HMOs to the non-fucosylated neutral HMOs in the mixture is from 4:1 to 1:1. In one or more examples, the method further includes administering the selected amount of the chosen one or more neutral HMOs for an initial treatment period of from 1 week to 8 weeks.

In some examples, the method further includes, after the initial treatment period, administering a daily dose of from 1 g to 5 g of the chosen one or more neutral HMOs for a maintenance period of at least 1 month.

Another method disclosed includes selecting a non-infant human patient who has been previously treated for one or more symptoms associated with irritable bowel syndrome (IBS). The method further includes selecting an amount of one or more human milk oligosaccharides (HMOs) chosen from 2'-fucosyllactose (2'-FL), 3-fucosyllactose (3-FL), difucosyllactose (DFL), lacto-N-fucopentaose I, lacto-N-tetraose (LNT), lacto-N-neotetraose (LNnT), and combinations thereof, the selected amount effective for increasing a relative abundance of *Bifidobacterium adolescentis* in the gastrointestinal microbiota of the non-infant human patient.

The method further includes, in various examples, increasing the relative abundance of *Bifidobacterium adolescentis* in the gastrointestinal microbiota of the non-infant human patient and reducing in the non-infant human patient a risk of re-occurrence of one or more symptoms associated with IBS by administering a daily dose of the amount of the chosen one or more neutral HMOs and optionally one or more excipients, to the non-infant human patient, wherein the daily dose of the mixture is from about 2.5 g to about 10 g.

In certain examples, the non-infant human patient has undergone treatment with an antibiotic and wherein the non-infant human patient has not consumed the antibiotic in a three-month period prior to the administering of the chosen one or more neutral HMOs. In certain examples, the method further includes reducing in the non-infant human patient the severity of one or more chronic symptoms selected from the following group: abdominal pain, abdominal discomfort, abdominal bloating, changes in bowel movement patterns, diarrhea, and constipation, by administering the selected amount of the chosen one or more neutral HMOs to the non-infant human patient.

In various examples, the method further includes reducing in the non-infant human patient the re-occurrence of one or more chronic symptoms selected from abdominal pain, abdominal discomfort, abdominal bloating, change in bowel movement patterns, diarrhea, and constipation, by administering the selected amount of one or more neutral HMOs to the non-infant human patient.

In various examples, the method further includes administering with the selected amount of the one or more neutral HMOs, one or more sialylated HMOs selected from 6'-sialyllactose (6'-SL) and 3'-sialyllactose (3'-SL). In some examples, administering the one or more neutral HMOs comprises administering a mixture of: one or more fucosylated neutral HMOs selected from 2'-FL, 3-FL, DFL, and LNFP-I; and one or more non-fucosylated neutral HMOs selected from LNT and LNnT.

In certain examples, a mass ratio of the fucosylated neutral HMOs to the non-fucosylated HMOs in the mixture is from 4:1 to 2:1. In some examples, the method further includes administering the mixture of the one or more neutral HMOs for a treatment period of from 1 week to 8 weeks. In various examples, the method further includes administering a daily dose of from 1 g to 5 g of the selected amount of the mixture of the one or more neutral HMOs for a maintenance period of at least 1 month.

A method, in accordance with one or more examples of the present disclosure includes selecting a non-infant human patient experiencing one or more symptoms associated with irritable bowel syndrome (IBS). The method further includes selecting an amount of one or more human milk oligosaccharides (HMOs) chosen from 2'-fucosyllactose (2'-FL), 3-fucosyllactose (3-FL), difucosyllactose (DFL), lacto-N-fucopentaose I, lacto-N-tetraose (LNT), lacto-N-neotetraose (LNnT), and combinations thereof, the selected amount effective for increasing a relative abundance of *Bifidobacterium adolescentis* in the gastrointestinal microbiota of the non-infant human patient; and increasing the relative abundance of *Bifidobacterium adolescentis* in the gastrointestinal microbiota of the non-infant human patient and reducing in the non-infant human patient the level of one or more inflammatory biomarkers or symptoms associated with the IBS by administering a daily dose of the selected amount of the chosen one or more neutral HMOs to the non-infant human patient.

In some examples, the one or more inflammatory biomarkers associated with the IBS are selected from tumor necrosis factor alpha (TNFα), interleukin 6 (IL-6), high-sensitivity C-reactive protein (hs-CRP), and lipopolysaccharide binding protein (LBP).

DETAILED DESCRIPTION

Reference throughout this specification to "one example," "an example," or similar language means that a particular feature, structure, or characteristic described in connection with the implementation is included in at least one example of the present disclosure. Thus, appearances of the phrases "in one example," "in an example," and similar language throughout this specification may, but do not necessarily, all refer to the same example.

INTRODUCTION

Gastrointestinal microbiota, the brain-gut axis, and mast cells may be implicated in the pathophysiology of IBS. The human gastrointestinal microbiota includes at least 1,000 species of bacteria, and about 1014 individual bacterial cells from about 160 different species inhabit each individual's intestine (Qin et al. Nature 464, 59 (2010)). An individual's genetic make-up and acquired immunity, as well as environmental factors, may influence their gastrointestinal microbiota. The microbiota in turn may shape the individual's immunity and physiology within the gastrointestinal system. A healthy individual may generally maintain a symbiotic relationship with the microbiota colonizing his/her intestines, while an individual with IBS may have an imbalance in this microbiota-immune interaction.

The gastrointestinal microbiota of IBS patients may be different from those of healthy controls. And gastrointestinal microbiota may cause post-infectious IBS (PI-IBS). Flagellin, the primary structural component of bacterial flagella may activate both the innate and adaptive immune system in individuals. For example, antibodies against bacteria flagellin (A4-F3a2 and Fla-X) have been detected more frequently in patients with IBS than in healthy controls (p=0.004 and p=0.009, respectively; Schoepfer et al. Neurogastroenterol. Motil. 20, 1110 (2008)). Also, individuals with post-infectious small intestine bacterial outgrowth (SIBO) associated with IBS may possess antibodies against flagellin proteins of the infecting bacteria (Spiller et al. Gastroenterology 136, 1979 (2009)). These bacteria are often *Campylobacter jejuni, Escherichia coli, Salmonella* enterilidis, and *Shigella flexneri.*

Treatments that target gastrointestinal microbiota such as antibiotics, probiotics and prebiotics appear to alleviate the symptoms of IBS; at least temporarily. For instance, the antibiotic rifaximin appears to reduce bacterial products that negatively affect the IBS patient.

Abdominal pain and discomfort associated with IBS is connected to the brain-gut axis and the response to stress hormones. IBS patients typically experience abnormal gut motility and visceral hypersensitivity mediated by the brain-gut axis or central stress response system. One arm of the brain-gut axis is the central efferent pathway, which is formed by the sympathetic nervous system and the hypothalamic-pituitary-adrenal axis (HPA). In stress-sensitive disorders including IBS, stress hormones of the HPA axis, such as adrenocorticotropic hormone (ACTH), cortisol, and catecholamine are released. The HPA axis response in IBS patients may be caused by increased mucosal immune activation, which in turn increases plasma cytokine levels to stimulate the HPA axis.

In addition to the gut microbiome and the gut-brain axis, the mast cells may also play an important role in the pathogenesis of IBS. Increased mast cell infiltration and activation in distal gut segments are associated with symptom onset and severity of IBS. These mast cells may also be implicated in the elevated response of visceral afferent nerves to mucosal stimulus in IBS patients. Mast cell hyperplasia may be commonly observed following infection by the bacteria mentioned above in both post-infectious IBS and non-post-infectious IBS.

In accordance with this disclosure, it has been surprisingly found that human milk monosaccharides (HMSs), advantageously sialic acid and/or fucose, and human milk oligosaccharides (HMOs), advantageously 2'-FL, 3-FL, LNT, LNnT, 3'-SL, 6'-SL, DFL, DSLNT and/or LNFP-I, are able to reduce chronic symptoms of irritable bowel syndrome in IBS patients, particularly those who are suffering from bacterial overgrowth, dysbiosis or an impaired mucosal barrier. Further, it has been found that HMSs/HMOs reduce the risk of re-occurrence of IBS in patients, particularly those who are suffering from bacterial overgrowth, dysbiosis or an impaired mucosal barrier. It is believed that the HMSs/HMOs can: (1) act as prebiotics to promote beneficial bacteria growth and reduce bacterial overgrowth and dysbiosis; (2) act as decoys for pathogens by binding to them and thereby reduce/prevent binding of the pathogens to epithelial cells in the gastrointestinal tract; (3) act to reduce chronic mucosal inflammation; and/or (4) repair damage to the mucosal barrier. The HMSs/HMOs can also act on neuronally dependent gut migrating motor complexes to address disorders of gut motility and possibly have beneficial effects on the central nervous systems of patients.

The term "oral administration" preferably means any conventional form for the oral delivery of a composition to a patient that causes the deposition of the composition in the gastrointestinal tract (including the stomach) of the patient. Accordingly, oral administration includes swallowing of composition by the patient, enteral feeding through a nasogastric tube, and the like.

The term "effective amount" preferably means an amount of a composition that provides a human milk monosaccharide or human milk oligosaccharide in a sufficient amount to render a desired treatment outcome in a patient. An effective amount can be administered in one or more doses to the patient to achieve the desired treatment outcome.

The term "human milk monosaccharide" or "HMS" preferably means a monosaccharide found in human breast milk. Examples include sialic acid and L-fucose. In human milk, the sialic acid is N-acetylneuraminic acid.

The term "human milk oligosaccharide" or "HMO" preferably means a complex carbohydrate found in human breast milk that can be in acidic or neutral form. More than about 200 different HMO structures are known to exist in human breast milk (Urashima et al.: Milk Oligosaccharides, Nova Biomedical Books, New York, 2011). HMOs can be backbone, fucosylated and sialylated oligosaccharides. Backbone HMOs consists of Glu, Gal and GlcNAc and are devoid of Fuc and sialic acid. Examples of backbone HMOs include lacto-N-tetraose (LNT), lacto-N-neotetraose (LNnT), lacto-N-neohexaose (LNnH) and lacto-N-hexaose (LNH). Fucosyl HMOs are fucosylated lactoses or fucosylated backbone HMOs such as 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose III (LNFP-III), fucosyl-para-lacto-N-neohexaose (F-pLNnH), lacto-N-difucohexaose I (LNDFH-I), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-lacto-N-hexaose III (FLNH-III) and fucosyl-para-lacto-N-neohexaose (F-pLNnH). Sialyl HMOs are sialylated lactoses or sialylated backbone HMOs such as 3',6-disialyllacto-N-tetraose (DSLNT), 6'-sialyllactose (6'-SL), 3'-sialyllactose (3'-SL), 6'-sialyllacto-N-neotetraose (LST c), 3'-sialyllacto-N-tetraose (LST a) and 6-sialyllacto-N-tetraose (LST b). HMOs containing both sialyl and fucosyl groups may be considered to belong to either of the latter two groups. Examples for sialyl and fucosyl HMOs include disialyl-fucosyl-lacto-N-hexaose II (DSFLNH-II), fucosyl-sialyl-lacto-N-neohexaose I (FSLNnH-I), fucosyl-sialyl-lacto-N-hexaose I (FSLNH-I) and 3-fucosyl-3'-sialyllactose (FSL).

The terms "microbiota", "microflora" and "microbiome" preferably mean a community of living microorganisms that typically inhabits a bodily organ or part. The most dominant members of the gastrointestinal microbiota include microorganisms of the phyla of Firmicutes, Bacteroidetes, Actinobacteria, Proteobacteria, Synergistetes, Verrucomicrobia, Fusobacteria, and Euryarchaeota; at genus level the microorganisms of *Bacteroides, Faecalibacterium, Bifidobacterium, Roseburia, Alistipes,* Collinsella, Blautia, *Coprococcus, Ruminococcus, Eubacterium* and Dorea; and at species level microorganisms of *Bacteroides uniformis, Alistipes putredinis,* Parabacteroides merdae, *Ruminococcus* bromii, Dorea longicatena, *Bacteroides* caccae, *Bacteroides* thetaiotaomicron, *Eubacterium hallii, Ruminococcus torques, Faecalibacterium prausnitzii, Ruminococcus* lactaris, Collinsella aerofaciens, Dorea formicigenerans, *Bacteroides* vulgatus and *Roseburia intestinalis.* In some instances, the gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

The terms "irritable bowel syndrome" and "IBS" preferably mean a group of functional bowel disorders of humans, particularly adults, characterized by one or more chronic symptoms including abdominal pain, abdominal discomfort, abdominal bloating, fatigue, and changes in bowel movement patterns, such as patterns of loose or more frequent bowel movements, diarrhoea, and constipation, typically in the absence of any apparent structural abnormality. There are at least three forms of IBS, depending on which symptom predominates: (1) diarrhoea-predominant (IBS-D); (2) constipation-predominant (IBS-C); and (3) IBS with alternating stool pattern (IBS-A or IBS-M). There are also various clinical subtypes of IBS, such as post-infectious IBS (IBS-PI).

The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry, LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 and WO 2007/101862 describe how to make core human milk oligosaccharides optionally substituted by fucose or sialic acid using genetically modified $E.\ coli$.

A synthetic composition of this disclosure comprising one or more human milk monosaccharides or one or more human milk oligosaccharides, or both can take any suitable form. For example, the composition can be in the form of a nutritional composition which contains other macronutrients such as proteins, lipids, or other carbohydrates. The synthetic composition can also be a pharmaceutical composition. In certain examples, the synthetic compositions contain one or more backbone HMOs and one or more fucosyl HMOs and optionally fucose. In some examples, the synthetic composition contains one or more backbone HMOs and one or more sialyl HMOs and optionally sialic acid. In various examples, the synthetic composition comprises one or more fucosyl HMOs and one or more sialyl HMOs, and optionally fucose and/or sialic acid, preferably both. In a preferred embodiment, the synthetic composition contains one or more backbone HMOs, one or more sialyl HMOs and one or more fucosyl HMOs, and optionally fucose and/or sialic acid, preferably both.

Nutritional Compositions

A nutritional composition of this disclosure can contain sources of protein, lipids and/or digestible carbohydrates and can be in powdered or liquid forms. The composition can be designed to be the sole source of nutrition or a nutritional supplement. For IBS patients, a nutritional supplement is preferred; especially a supplement which can form a meal or snack replacement. Preferably the nutritional composition is lactose-reduced or, better yet, lactose-free. Preferably, the nutritional composition is also free from, or low in amounts of, FODMAP carbohydrates.

Suitable protein sources include milk proteins, soy protein, rice protein, pea protein and oat protein, or mixtures thereof. Milk proteins can be in the form of milk protein concentrates, whey protein or casein, or mixtures of both. Soy, rice, pea, and oat protein can be in the form or protein isolated. The protein can be whole protein or hydrolysed protein, either partially hydrolysed or extensively hydrolysed. The protein can provide about 5% to about 50%, preferably about 10% to 30%, of the energy of the nutritional composition. The protein source preferably is not a source of non-fermentable carbohydrates such as lactose. Therefore, if a milk protein is used as the protein source, the milk protein is preferably lactose-reduced or lactose-free.

Suitable digestible carbohydrates include maltodextrin, hydrolysed or modified starch or corn starch, glucose polymers, corn syrup, corn syrup solids, tapioca, sucrose, and glucose, or mixtures thereof. Generally digestible carbohydrates provide about 35% to about 75%, preferably about 45% to 70%, of the energy of the nutritional composition. Preferably the digestible carbohydrate is free from lactose.

Suitable lipids include rapeseed oil, sunflower seed oil, palm oil, soy oil, milk fat, corn oil and soy lecithin. Long-chain poly unsaturated fatty acids (LC-PUFA), especially omega-3 fatty acids such as docosahexaenoic acid (DHA), can be included in the lipid source because they have anti-inflammatory properties. Suitable sources of LC-PUFA are plant oils, marine plankton oils, fungal oils, and fish oils. The lipid source can also include medium chain triglycerides (MCT). Fractionated coconut oils are a suitable source of medium chain triglycerides. The lipid source preferably provides about 5% to about 25% of the energy of the nutritional composition; for example, about 10% to 20%. The lipid content is preferably reduced because high fat diets can provoke IBS symptoms.

The nutritional composition preferably also includes vitamins and minerals. If the nutritional composition is intended to be a sole source of nutrition, it preferably includes a complete vitamin and mineral profile. Examples of vitamins include Vitamins A, B-complex (such as B1, B2, B6 and B12), C, D, E and K, niacin, and acid vitamins such as pantothenic acid and folic acid and biotin. Examples of minerals include calcium, iron, zinc, magnesium, iodine, copper, phosphorus, manganese, potassium, chromium, molybdenum, selenium, nickel, tin, silicon, vanadium, and boron.

The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 g/ml of lutein. Lycopene can be included in an amount from about 0.001 µg/ml to about 10 µg/ml, preferably about 0.0185 mg/ml to about 5 g/ml of lycopene. Beta-carotene can comprise from about 0.001 µg/ml to about 10 mg/ml, for example about 0.034 µg/ml to about 5 µg/ml of beta-carotene.

The nutritional composition can also contain various other conventional ingredients such as preservatives, emulsifying agents, thickening agents, buffers, fibres and probiotics, especially probiotics which can help to reduce symptoms in IBS patients (e.g. VSL #3, $B.\ infantis$ 35624, $B.\ animalis$ subsp. $lactis$ BB-12, $B.\ lactis$ Bi-07, $L.\ rhamnosus$ GG, $L.\ rhamnosus$ Lc705, $L.\ plantarum$ DSM 9843, $L.\ plantarum$ CECT7484, $L.\ plantarum$ CECT7485, $L.\ acidophilus$ NCFM, $L.\ fermentum$ CECT5716, $B.\ breve$ Bb99, $Propionibacterium$ freundenreichii ssp. $Shermanii$ JS, $P.\ acidilactici$ CECET7483, $Streptococcus\ faecium$), antioxidant/anti-inflammatory compounds including tocopherols, carotenoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilizers, lubricants, and so forth.

The nutritional composition can be in the form of a soluble powder, a liquid concentrate, or a ready-to-use formulation. Various flavours, fibres and other additives can also be present.

The nutritional compositions can be prepared by any commonly used manufacturing techniques for preparing nutritional compositions in solid or liquid form. For example, the composition can be prepared from various feed solutions. A protein-in-fat feed solution can be prepared by heating and mixing the lipid source and then adding an emulsifier (e.g., lecithin), fat soluble vitamins, and at least a portion of the protein source while heating and stirring.

A carbohydrate feed solution is also prepared by adding minerals, trace, and ultra trace minerals, thickening or suspending agents to water while heating and stirring. The resulting solution is held for 10 minutes with continued heat and agitation before adding carbohydrates (e.g., the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified, and homogenized, and then allowed to cool. Water soluble vitamins and ascorbic acid are added, the pH is adjusted to the desired range, if necessary, flavours are added, and water is added to achieve the desired total solid level.

For a liquid product, the resulting solution can then be aseptically packaged to form an aseptically packaged nutritional composition. In this form, the nutritional composition can be in ready-to-feed or concentrated liquid form. Alternatively, the composition can be spray dried and processed and packaged as a reconstitutable powder.

When the nutritional product is a ready-to-feed nutritional liquid, the total concentration of HMS/HMOs in the liquid, by weight of the liquid, is from about 0.0001% to about 2.0%, including from about 0.001% to about 1.5% and from about 0.01% to about 1.0%; or from about 0.002% to about 3.0%, including from about 0.005% to about 2% and from about 0.05% to about 1.0%. When the nutritional product is a concentrated nutritional liquid, the total concentration of HMS/HMOs in the liquid, by weight of the liquid, is from about 0.0002% to about 4.0%, including from about 0.002% to about 3.0% and from about 0.02% to about 2.0%; or from about 0.004% to about 6.0%, including from about 0.01% to about 4.0% and from about 0.1% to about 2.0%.

Unit Dosage Forms

The synthetic composition of this disclosure can also be in a unit dosage form such as a capsule, tablet, or sachet. For example, the composition can be in a tablet form comprising the human milk monosaccharides and/or oligosaccharides, and one or more additional components to aid formulation and administration, such as diluents, excipients, antioxidants, lubricants, colorants, binders, disintegrants, and the like.

Suitable diluents, excipients, lubricants, colorants, binders, and disintegrants include polyethylene, polyvinyl chloride, ethyl cellulose, acrylate polymers and their copolymers, hydroxyethyl-cellulose, hydroxypropylmethyl-cellulose (HPMC), sodium carboxymethylcellulose, polyhydroxyethyl methacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQlO") and glutathione.

The unit dosage forms, especially those in sachet form, can also include various nutrients including macronutrients.

Administration Dosing

For reducing IBS symptoms in a patient having bacterial overgrowth, dysbiosis and/or an impaired mucosal barrier, the amount of HMS(s) and/or HMO(s) required to be administered to the patient will vary depending upon factors such as the risk and severity of the disease, the age of the patient, the form of the composition, and other medications being administered to the patient. However, the required amount can be readily determined by a medical practitioner and would generally be in the range of about 20 mg to about 20 g per day, in certain embodiments preferably about 50 mg to about 10 g per day, more preferably from about 100 mg to about 7.5 g per day, even more preferably from about 500 mg to about 5 g per day, especially from about 1 g to about 2.5 g per day; in other embodiments preferably about 50 mg to about 20 g per day, more preferably from about 100 mg to about 15 g per day, even more preferably from about 500 mg to about 10 g per day, especially from about 1 g to about 7.5 g per day.

During an initial treatment phase, the dosing can be higher; for example, 100 mg to 20 g or 100 mg to 30 g per day, preferably 500 mg to 15 g per day, more preferably 1 g to 10 g per day, in certain embodiments 2.5 g to 7.5 g per day. During a secondary prevention phase, the dosing can be reduced; for example, in certain embodiments, to 20 mg to 10 g per day, preferably to 100 mg to 7.5 g per day, more preferably to 500 mg to 2.5 g per day, even more preferably to 750 mg to 1.5 g per day, or, in other embodiments, to 20 mg to 20 g per day, preferably to 100 mg to 10 g per day, more preferably to 500 mg to 7.5 g per day, even more preferably to 750 mg to 5 g per day.

The present disclosure may be implements in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

EXAMPLES

Examples are now described to illustrate further aspects of the disclosed methods.

Example 1—Human Trial

A total of 60 male and female IBS patients are recruited to participate in the study. After a screening visit and run-in period of 1-2 weeks, the patients are selected. The patients are randomized into three groups, each of 20 patients, with two groups consuming the treatment product and one group the placebo product for 8 weeks. The treatment product contains either 5 or 10 grams of a combination of 2'-FL, LNnT, LNT, 3-FL, 6'-SL and 3'-SL while the control product contains 2 grams glucose. Both products are in powder form in a unit dosage container.

The patients are eligible to participate if they are at least 18 years of age, meet the Rome III criteria for IBS, and are diagnosed with bacterial overgrowth/dysbiosis. All recruited patients are able and willing to understand and comply with the study procedures. Patients are excluded if: they have participated in a clinical study one month prior to screening visit; they have abnormal results in the screening tests which are clinically relevant for study participation; they are suffering for a severe disease such as malignancy, diabetes, severe coronary disease, kidney disease, neurological disease, or severe psychiatric disease or any condition which can confound the results of the study; used highly dosed probiotic supplements (yoghurt allowed) for 3 months prior to the study; consumed antibiotic drugs 3 months prior to the study; consumed on a regular basis any medication that might interfere with symptom evaluation 2 weeks prior to the study; and pregnant or lactating.

At the screening visit, medical history and concomitant medication is registered and a blood sample for safety analyses is collected. A faecal sample kit is distributed. Patients are instructed to keep their samples in the freezer until the next visit.

At the second visit, eligibility criteria are checked and eligible subjects are randomized to the three arms in the trial. The faecal samples are collected and equipment for new samples are distributed. Patients are familiarized with an interactive internet enabled system which records data daily and are provided with either treatment or control products. Subjects are reminded not to change their usual diet during the study. Blood samples are collected for biomarker studies.

The serum from the blood samples is transferred to cryotubes and stored at −80° C. The following biomarkers are measured: aldosterone, angiotensin II, apolipoprotein A1 (ApoA1), apolipoprotein B (ApoB), blood urea nitrogen, iron, BNP brain natriuretic peptide (BNP), cortisol, eosinophilic cationic protein (ECP), estradiol, aliphatic carboxylate, free fatty acid (FFA), glucagon, HbA1c, IgA, IgM, IgG, IL-10, IL-6, insulin, lysozyme, progesterone, testosterone, TNF-α, transferrin, vitamin A, vitamin B1, vitamin B12, vitamin B6, vitamin D, vitamin K1, A-1-antitrypsin.

The faecal samples are stored at −80° C. until analysis. Faecal samples are subjected to 16 S RNA sequencing analysis.

The study runs for 8 weeks with the patients consuming either a placebo or a treatment product daily. Patients are instructed to consume the products in the morning with breakfast. Compliance is monitored through the interactive internet enabled system. The patients also use the system to record:

Bristol Stool Form Scale (BSF) Information

Symptom information such as abdominal pain, abdominal discomfort, abdominal cramping, abdominal bloating, and abdominal fullness, Additional Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

At the end of the study, each patient has an exit visit with the medical team. Faecal samples and blood samples are collected and analysed as before.

The treatment patients report a reduction in pain and an improvement in bowel movement as compared to the placebo group. The blood biomarker analysis indicates that the treatment patients have reduced levels of inflammatory markers. The faecal analysis indicates that the treatment patients have reduced levels of bacterial overgrowth/dysbiosis.

Example 2—Human Trial

A total of 300 male and female IBS patients are recruited to participate in the study. After a screening visit and run-in period of 1-2 weeks, the patients are selected. The patients are randomized into two groups, each of 150 patients, with one group consuming the treatment product and one group the placebo product for 8 weeks. The treatment product contains 5 grams of a combination of 2'-FL and LNnT while the control product contains 2 grams glucose. Both products are in powder form in a unit dosage container.

The patients are eligible to participate if: they are between 18 and 60 years of age; meet the Rome III criteria for IBS; report a weekly average of worst daily abdominal pain intensity score of >3 on a 0-10 point scale; report a pain/discomfort frequency of at least 2 days a week during screening evaluation; report fewer than three complete spontaneous bowel movements (CSBMs) per week for IBS-C subgroup of patients; and at least one stool with a consistency of Type 6 or Type 7 Bristol stool (BSS) on at least 2 days per week for IBS-D subgroup of patients. All recruited patients are able and willing to understand and comply with the study procedures. Patients are excluded if: they have participated in a clinical study one month prior to screening visit; they have abnormal results in the screening tests which are clinically relevant for study participation; they are suffering for a severe disease such as malignancy, diabetes, severe coronary disease, kidney disease, neurological disease, or severe psychiatric disease or any condition which can confound the results of the study; used highly dosed probiotic supplements (yoghurt allowed) for 3 months prior to the study; consumed antibiotic drugs 3 months prior to the study; consumed on a regular basis any medication that might interfere with symptom evaluation 2 weeks prior to the study; and pregnant or lactating.

At the initial visit (screening), each patient is given both written and oral information about the study and the patient is asked to sign an informed consent form.

Patients are evaluated by a full review of clinical history, and based on clinical symptoms, characterized into one of the three following groups; diarrhoea predominant (IBS-D), constipation predominant (IBS-C) or alternating/mixed (IBS-A/M). This enables allocation of patients into subgroups at post-analysis.

A blood sample for eligibility analysis is collected. A talk through of the electronic questionnaires (GSRS, IBS-SSS, QoL and BSFS) is performed to familiarize the patients with the electronic system, and equipment for faecal sampling is distributed to each patient. Patients are instructed to keep their samples in the freezer until the next visit.

At the second visit (beginning of intervention), eligibility criteria are checked and eligible subjects are randomized to the two arms in the trial. Symptoms (as measured by GSRS, IBS-SSS, BSFS and QoL scales) are assessed. Trial supplementation is distributed along with instructions on use of an electronic compliance diary. The faecal samples are collected and equipment for collecting new samples are distributed. Patients are reminded not to change their usual diet during the study.

Blood samples are collected for biomarker studies and biobanking. The serum from the blood samples is transferred to cryotubes and stored at −80° C. The following biomarkers are measured TNF-α, IL-8, IL-6, IL-12, IL-10, hs-CRP, lipopolysaccharide binding protein, tryptase, antiflagellin, zonulin, histamine, prostaglandin 2, and cortisol.

The faecal samples are stored at −80° C. until analysis. Microbiological analysis is performed on the faecal samples using the 16S rRNA gene sequence.

The study runs for 8 weeks with the patients consuming either a placebo or a treatment product daily. Patients are instructed to consume the products in the morning with breakfast. Compliance is monitored through the interactive internet enabled system. The patients also use the system to record:

Bristol Stool Form Scale (BSFS) information,
Symptom information such as abdominal pain, abdominal discomfort, abdominal cramping, abdominal bloating, and abdominal fullness,
Quality of life (QoL) information,
IBS severity scoring system (IBS-SSS) information,
Additional Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

4 weeks after commencement, there is an intermediate check. A physical examination is done and symptoms (as measured by GSRS, IBS-SSS, BSFS and QoL scales etc.) are reassessed. Faecal samples and blood samples are collected and analysed as before, and equipment for collection of new faecal samples are distributed.

At the end of the intervention (8 weeks), each patient has a visit with the medical team. A physical examination is done and symptoms (as measured by GSRS, IBS-SSS, BSFS and QoL scales etc.) are reassessed. Trial supplementation products are collected to check compliance. Faecal samples and blood samples are collected and analysed as before.

At this visit, the participants are asked if they wish to continue in an open label follow up study. Fifty percent of the participants continuing are given half the dose of the active product and the rest are not taking the product. The patients agreeing to continue are given equipment for faecal sample collection and for the patients continuing on active product, trial supplementation is distributed.

At the end of the study, the patients have a final visit where faecal samples are collected and symptoms (as measured by GSRS, IBS-SSS, BSFS and QoL scales) are reassessed from the patients of the open label follow-up study. Additionally, they are asked about any adverse events.

For patients not participating in the open label follow up study, this visit will only be relevant, if they have adverse events. This visit may be completed via telephone. The treatment patients report a reduction in pain/visceral sensitivity and an improvement in bowel movement as compared to the placebo group. The blood biomarker analysis indicates that the treatment patients have reduced levels of inflammatory markers, reduced gut permeability indicating an improved mucosal barrier, and reduced evidence of mast cell degranulation. The faecal analysis indicates that the treatment patients have reduced levels of bacterial overgrowth/dysbiosis and a higher level of Bifidobacteria; especially *Bifidobacterium adolescentis*.

Example 3—Nutritional Composition

A ready to feed nutritional composition is prepared from water, maltodextrin, corn syrup, sugar, milk protein concentrate, vegetable oil (canola, high oleic sunflower and corn), soy protein isolate, acacia gum, flavours, HMOs, potassium citrate, magnesium phosphate, cellulose gel and gum, calcium carbonate, sodium ascorbate, soy lecithin, choline bitartrate, calcium phosphate, alpha-tocopheryl acetate, ascorbic acid, carrageenan gum, ferric pyrophosphate, flavours, sweeteners (*Stevia*), vitamin A palmitate, niacinamide, vitamin D3, calcium pantothenate, manganese sulphate, copper sulphate, pyridoxine hydrochloride, thiamine hydrochloride, beta carotene, riboflavin, chromium chloride, folic acid, biotin, potassium iodide, phytonadione, sodium selenite, sodium molybdate, vitamin B12.

The composition provides a nutritional supplement which is a good source of protein, low in fat, vitamins, minerals, and antioxidants, and meets FODMAP criteria. Further, the composition contains HMO's which are able to promote the growth of beneficial intestinal bacteria and modulate chronic inflammation.

Example 4—Capsule Composition

A capsule is prepared by filling about 1 g of HMS/HMO into a 000 gelatine capsule using a filing machine. The capsules are then closed. The HMS/HMO are in free flowing, powder form.

Example 5—Mucosal Barrier Function

2'-FL and LNnT are tested with respect to their ability to induce MUC2, TFF3, EIMβ, CHST5, and GAL3 ST2 expression in the human LS174T cell culture model of goblet cells. The human LS174T cell line is obtained from the American Type Culture Collection (ATCC). LS174T cells are maintained in minimum essential medium (MEM) supplemented according to instructions at 37° C. in 5% CO2. 2'-FL and LNnT are dissolved in cell culture grade water to the required concentration. The LS174T cells are treated with the HMO solution containing 0 or 5 mg HMO/ml.

The LS174T cells are collected and suspended in Trizol reagent and total RNA is isolated using an RNA analysis kit (Qiagen) according to the manufacturer's instructions and the RNA isolates are quantified using Nanodrop analysis (Thermo Fisher Scientific). RNA isolates are reverse transcribed using a high-capacity cDNA Reverse Transcription Kit (Applied Biosystems) to create cDNA, which is then used to assess gene expression via quantitative RT-PCR.

For the quantitative RT-PCR, specific TaqMAN gene expression assays are obtained from Applied Biosystems, which include expression assays for MUC2, TFF3, CHST5 and GAL3ST2. Quantitative real-time PCR is performed using TaqMAN PCR Master Mix (Applied Biosystems). Reactions are run in duplicates in a 384-well plate using an Applied Biosystems 7900HT Fast Real-Time PCR System. The results are analysed using SDS 2.3 software and calculated by delta delta Ct method. All samples are normalized to Gus-β expression and fold induction is calculated over untreated controls. Gene expression is expressed as fold increase compared to HMO-free control cells. The experiment is repeated three times.

The results indicate that treatment with 2'-FL and LNnT increases the expression of the MUC2 and TFF3 genes compared to control cultures. Increased expression of goblet cell genes is specific and not universal, as evidenced by the minimal induction or lack of induction of CHST5 and GAL3 ST2, respectively. MUC2 and TFF3 are key components of the mucosal barrier and improve mucosal barrier function.

What is claimed is:

1. A method comprising:
   selecting a non-infant human patient with irritable bowel syndrome (IBS) experiencing one or more IBS symptoms;
   selecting an amount of one or more neutral human milk oligosaccharides (HMOs) selected from the group consisting of 2'-fucosyllactose (2'-FL), 3-fucosyllactose (3-FL), difucosyllactose (DFL), lacto-N-fucopentaose I (LNFP-I), lacto-N-tetraose (LNT), lacto-N-neotetraose (LNnT), and combinations thereof, the amount effective for increasing a relative abundance of *Bifidobacterium adolescentis* in the gastrointestinal microbiota of the non-infant human patient; and increasing the relative abundance of *Bifidobacterium adolescentis* in the gastrointestinal microbiota of the non-infant human patient and reducing the likelihood of the non-infant human patient experiencing the one or more IBS symptoms by administering a daily dose of the selected amount of the one or more neutral HMOs to the non-infant human patient, wherein the daily dose is from about 2.5 g to about 10 g.

2. The method of claim 1, wherein the non-infant human patient has undergone treatment with an antibiotic to reduce bacteria that negatively affect the IBS, and wherein the non-infant human patient has not consumed the antibiotic in a three-month period prior to the administering of the one or more neutral HMOs.

3. The method of claim 1, wherein the one or more IBS symptoms are chronic symptoms selected from the group consisting of abdominal pain, abdominal discomfort, abdominal bloating, change in bowel movement patterns, diarrhea, and constipation.

4. The method of claim 1, further comprising administering with the selected amount of the one or more neutral HMOs, one or more sialylated HMOs selected from the group consisting of 6'-sialyllactose (6'-SL) and 3'-sialyllactose (3'-SL).

5. The method of claim 1, wherein administering the one or more neutral HMOs comprises administering a mixture of:
one or more fucosylated neutral HMOs selected from the group consisting of 2'-FL, 3-FL, DFL, and LNFP-I; and
one or more non-fucosylated neutral HMOs selected from the group consisting of LNT and LNnT.

6. The method of claim 1, wherein the mass ratio of the fucosylated neutral HMOs to the non-fucosylated neutral HMOs in the mixture is from 4:1 to 1:1.

7. The method of claim 1, further comprising administering the selected amount of the one or more neutral HMOs for an initial treatment period of from 1 week to 8 weeks.

8. The method of claim 7, further comprising, after the initial treatment period, administering a daily dose of from 1 g to 5 g of the one or more neutral HMOs for a maintenance period of at least 1 month.

9. A method comprising:
selecting a non-infant human patient who has been previously treated for one or more symptoms of irritable bowel syndrome (IBS);
selecting an amount of one or more human milk oligosaccharides (HMOs) selected from the group consisting of 2'-fucosyllactose (2'-FL), 3-fucosyllactose (3-FL), difucosyllactose (DFL), lacto-N-fucopentaose I (LNFP-I), lacto-N-tetraose (LNT), lacto-N-neotetraose (LNnT), and combinations thereof, the selected amount effective for increasing a relative abundance of *Bifidobacterium adolescentis* in the gastrointestinal microbiota of the non-infant human patient; and
increasing the relative abundance of *Bifidobacterium adolescentis* in the gastrointestinal microbiota of the non-infant human patient and reducing in the non-infant human patient a risk of re-occurrence of one or more symptoms associated with IBS by administering a daily dose of the amount of the one or more neutral HMOs and optionally one or more excipients, to the non-infant human patient, wherein the daily dose is from about 2.5 g to about 10 g.

10. The method of claim 9, wherein the non-infant human patient has undergone treatment with an antibiotic and wherein the non-infant human patient has not consumed the antibiotic in a three-month period prior to the administering of the one or more neutral HMOs.

11. The method of claim 9, further comprising reducing in the non-infant human patient the severity of one or more chronic symptoms selected from the group consisting of: abdominal pain, abdominal discomfort, abdominal bloating, changes in bowel movement patterns, diarrhea, and constipation, by administering the selected amount of the one or more neutral HMOs to the non-infant human patient.

12. The method of claim 9, further comprising reducing in the non-infant human patient the re-occurrence of one or more chronic symptoms selected from the group consisting of abdominal pain, abdominal discomfort, abdominal bloating, change in bowel movement patterns, diarrhea, and constipation, by administering the selected amount of the one or more neutral HMOs to the non-infant human patient.

13. The method of claim 12, further comprising administering with the selected amount of the one or more neutral HMOs, one or more sialylated HMOs selected from the group consisting of 6'-sialyllactose (6'-SL) and 3'-sialyllactose (3'-SL).

14. The method of claim 9, wherein administering the one or more neutral HMOs comprises administering a mixture of:
one or more fucosylated neutral HMOs selected from the group consisting of 2'-FL, 3-FL, DFL, and LNFP-I; and
one or more non-fucosylated neutral HMOs selected from the group consisting of LNT and LNnT.

15. The method of claim 9, wherein a mass ratio of the fucosylated neutral HMOs to the non-fucosylated HMOs in the mixture is from 4:1 to 2:1.

16. The method of claim 9, further comprising administering the mixture of the one or more neutral HMOs for a treatment period of from 1 week to 8 weeks.

17. The method of claim 9, further comprising administering a daily dose of from 1 g to 5 g of the selected amount of the mixture of the one or more neutral HMOs for a maintenance period of at least 1 month.

18. A method comprising:
selecting a non-infant human patient experiencing one or more symptoms of irritable bowel syndrome (IBS);
selecting an amount of one or more human milk oligosaccharides (HMOs) selected from the group consisting of 2'-fucosyllactose (2'-FL), 3-fucosyllactose (3-FL), difucosyllactose (DFL), lacto-N-fucopentaose I, lacto-N-tetraose (LNT), lacto-N-neotetraose (LNnT), and combinations thereof, the selected amount effective for increasing a relative abundance of *Bifidobacterium adolescentis* in the gastrointestinal microbiota of the non-infant human patient; and
increasing the relative abundance of *Bifidobacterium adolescentis* in the gastrointestinal microbiota of the non-infant human patient and reducing in the non-infant human patient the level of one or more inflammatory biomarkers or symptoms associated with the IBS by administering a daily dose of the selected amount of the one or more neutral HMOs to the non-infant human patient, wherein the daily dose is from about 2.5 g to about 10 g.

19. The method of claim 18, wherein the one or more inflammatory biomarkers associated with the IBS are selected from the group consisting of tumor necrosis factor alpha (TNFα), interleukin 6 (IL-6), high-sensitivity C-reactive protein (hs-CRP), and lipopolysaccharide binding protein (LBP).

* * * * *